United States Patent [19]
Mast

[11] Patent Number: 5,269,784
[45] Date of Patent: Dec. 14, 1993

[54] SCREW NUT FOR PLATE OSTEOSYNTHESIS

[75] Inventor: Jeffrey W. Mast, Grosse Pointe Park, Mich.

[73] Assignee: Synthes (U.S.A.), Paoli, Pa.

[21] Appl. No.: 833,038

[22] Filed: Feb. 10, 1992

[30] Foreign Application Priority Data

Dec. 10, 1991 [CH] Switzerland .................. 3634/91

[51] Int. Cl.$^5$ ............................................. A61B 17/58
[52] U.S. Cl. .................................... 606/69; 606/73; 606/71
[58] Field of Search ............................ 606/69–73, 606/78, 60, 66, 67, 68; 403/408.1, 283; 411/432, 177, 179, 184, 187

[56] References Cited

U.S. PATENT DOCUMENTS

| | | | |
|---|---|---|---|
| 2,355,679 | 11/1942 | Roxs | 411/432 |
| 3,977,397 | 8/1976 | Kalnberz | 606/56 |
| 4,013,071 | 3/1977 | Rosenberg | 606/73 |
| 4,027,711 | 6/1977 | Tummarello | 411/172 |
| 4,263,904 | 4/1981 | Judet | 606/69 X |
| 4,388,921 | 6/1983 | Sutter et al. | 606/71 |
| 4,484,570 | 11/1984 | Sutter et al. | 606/72 |
| 4,794,918 | 1/1989 | Wolter | 606/72 X |
| 4,834,752 | 5/1989 | Van Kampen | 606/77 X |
| 4,880,343 | 11/1989 | Matsumoto | 411/303 |
| 4,887,595 | 12/1989 | Heinig et al. | 606/73 X |
| 4,964,403 | 10/1990 | Karás et al. | 606/73 X |
| 4,988,351 | 1/1991 | Paulos et al. | 606/72 |
| 5,041,113 | 8/1991 | Biedermann et al. | 606/71 X |
| 5,053,036 | 10/1991 | Perren et al. | 606/69 |
| 5,057,111 | 10/1991 | Park | 606/69 |
| 5,085,660 | 2/1992 | Lin | 606/72 |

FOREIGN PATENT DOCUMENTS

| | | | |
|---|---|---|---|
| 481639 | 1/1970 | Switzerland | 606/67 |
| 1326260 | 7/1987 | U.S.S.R. | 606/67 |
| 370948 | 4/1932 | United Kingdom | 411/177 |
| 646210 | 11/1950 | United Kingdom | 411/177 |

OTHER PUBLICATIONS

Vitallium Surgical Appliances, Mar. 1948.

*Primary Examiner*—Robert A. Hafer
*Assistant Examiner*—David J. Kenealy
*Attorney, Agent, or Firm*—Davis Hoxie Faithfull & Hapgood

[57] ABSTRACT

This screw nut (1) is designed for the rigid fixation of a bone screw (15) to a bone plate (20) having plate holes (21). It has a generally cylindrical body (5,6) with a central axis (2), a central hole (3) with a hole axis (34) and an internal thread (4) designed to receive a bone screw (15). The body (5,6) comprises of a lower section (5), an upper section (6), a lower side (9) and an upper side (10). The profile (7) of the upper section (6) orthogonal to said hole axis (34) is smaller than the profile (8) of the lower section (5) orthogonal to said hole axis (34) and the upper section (6) is shaped to be insertable into the plate hole (21) of the bone plate (20).

19 Claims, 4 Drawing Sheets

SCREW NUT FOR PLATE OSTEOSYNTHESIS

BACKGROUND OF THE INVENTION

1. Field of the Invention

The invention relates generally to a screw nut for the rigid fixation of a bone screw to a bone plate having plate holes, whereby the screw nut has a generally cylindrical body with a central axis, a central hole with a hole axis and an internal thread designed to receive said bone screw, a lower section, an upper section, a lower side and an upper side.

2. Description of the Prior Art

Stable fixation is a prerequisite for successful treatment of complex deformity, nonunion, and fracture. Unfortunately, not all situations allow for the application of basic principles, namely creating a construct inherently stable enough so that the bone protects the implant. Osteoporotic bone or bone with abnormally thinned cortices due to failed fixation or previous infection may not allow lasting screw purchase, thus stability gained by applying compression across the fracture site is quickly lost as the thin bone resorbs around the screws. This loss of compression is rapid, since loosening of the screws allows early toggling at the plate/screw interface.

Most types of bone plates which are commonly used in osteosynthesis are fixed solely by means of bone screws to the bone. Since the bone screws are only secured to bone, there is no rigid fixation thereof to the bone plate. Therefore a loosening of the bone screws in the bone or a resorption of the bone can easily lead to a loosening of the bone plate.

It is already known in plate osteosynthesis that a screw nut may be used on the opposite cortex to fix the screw and therefore, the plate to the bone. This method does not produce a direct fixation between bone screws and plate, but only compression of the bone located between the screw nut and the plate and perforated by the bone screw.

In a variety of situations it is desirable to achieve a rigid fixation between bone screws and bone plate in order to avoid subsequent loosening. It is already known from EP-A 340.223 to anchor by means of frictional adhesion alone a bone screw with a specially designed conical head in a bone plate having corresponding conical holes. In this prior art device both holes and screw heads must conform to a specific taper of the conical configuration in order to obtain a rigid fixation between them.

It is also known from the EP-A 340.223 that the projections on the underside of the bone plate reduces the surface area coming into contact with the bone and produces a theoretical improvement in vascularity to the bone. Projections and bone plate are forming, however, an inseparable unit, which can only be used as such and which does not allow for any individual adaptation.

Therefore, the known prior art devices do not offer the versatility sometimes required for optimal treatment in plate osteosynthesis.

The present invention addresses the problems associated with the prior art devices and provides for maximum versatility and adaptability and accomplishes this with a single component device which can be used with any type of bone plate and bone screw and at any selected position (hole) of the plate and which fixes the screw to the plate and acts as a distance holder for reducing the contacting area between bone plate and bone.

SUMMARY OF THE INVENTION

It is an object of the present invention to provide improved versatility and adaptability in plate osteosynthesis with a rigid connection between bone screws and bone plate.

This and other objects are achieved in accordance with the present invention by a unique screw nut which includes two differently shaped sections, an upper and a lower one, whereby the profile of said upper section orthogonal to said hole axis is smaller than the profile of said lower section orthogonal to said hole axis and said upper section is shaped to be insertable into said plate hole of said bone plate.

The upper section of the screw nut according to the invention can be shaped in different ways, as long as it is insertable into the plate hole. Preferably the profile of the upper section orthogonal to the central axis should match the typical plate hole geometry, i.e., should by elliptical with round or flat sides. This profile blocks rotation of the screw nut in the plate hole around the central axis. The axial height of the upper section of the screw nut should be designed in such a way that it can be lodged completely within the plate hole.

In one embodiment of the invention the under side located in the lower section has sharp projections. These projections block the rotation of the screw nut; and on the other hand enhance the friction between the device and the bone; and contribute to a further reduction of the contact area to the bone by slightly elevating the underside of the lower portion of the device from the bony surface.

In a further embodiment the screw nut according to the invention consists of two parts. The lower section and the upper section are two separate elements connected to each other by a simple bearing or thread which allows rotation to said central axis. By this construction it is possible to avoid the transfer of undesired rotational moments to the bone occurring in the final phase of tightening the screw nut.

The internal thread of the screw nut must obviously conform to the external thread of the screws to be used; preferably it is made of metal but all or part may be made of plastics, preferably in the form of a hollow cylindrical insert which is lodged in the metallic body of the screw nut.

In a further embodiment the screw nut consists of a memory alloy which adopts a smaller volume when heated from lower temperatures to body temperature. The screw nut made of this material is used for fixation at a relatively low temperature and clamps in a very effective manner after becoming heated to the body temperature.

When the screw nut according to the invention is used for bone plates having circular holes, like buttress plates, the upper section of the screw nut cannot be blocked in rotation as in elliptical holes. In order to alleviate this short-coming in a further embodiment the lower section is provided with projections, preferably in the form of shims or pins, at its free upper side. Thanks to these projections, which upon tightening of the screw nut impinge into the underside of the bone plate, the rotational blocking is achieved.

Both type of projection, those on the underside as well as those on the upper side may be located asymmetrically or symmetrically around the central axis in order to achieve a desired anchoring. In the case of sharp projections they may be staggered by 120°.

When using ordinary bone screws whose external thread ends at a certain distance from the screw head it has proved to be of benefit to insert a bushing between the head of the bone screw and the upper side of the bone plate.

The advantages of the screw nut according to the invention reside primarily in its universal applicability since it can be used together with any type of bone plates and screws. It may be used selectively at single positions (holes) of the bone plate, respectively with single bone screws inserted therein. It is possible therefore to decide about the use of the screw nut intraoperatively at any phase of the operation.

A further advantage of the screw nut is its function as distance holder between the bone plate and the bone. The reduced contact area to the bone allows for a theoretical improvement of blood perfusion in the bone and accelerated healing.

By holding the plate away from the bony surface, the screw nut minimizes the vascular disruption that would otherwise occur while still providing rigid fixation. Preservation of blood supply avoids the sequence of events that lead to impaired remodelling and increased porosity beneath a plate.

Thanks to the rigid fixation between bone screws and plate achieved by the use of the screw nut it is possible to position the bone plate at a defined distance from the bone, such as to produce an ultra-low profile, external fixator. Those regions of the bone not in contact with the plate will potentially avoid the cortical vascular disruption that occurs when a plate is firmly fixed to a bone. This facilitates bone healing and remodelling.

The rigid fixation prevents the undesired occurrence of deformities as may arise with axial compression because under other circumstances other screws may fit in the hole of the plate.

The nut can also help to salvage a hole that has been inadvertently rendered incapable of providing screw purchase. For example, when a screw breaks in the bone and subsequent removal results in an enlarged hole at the near cortex, replacement with a new screw in the same hole would result in less stable fixation not only due to the loss of one cortex, but also due to toggle that is allowed to occur at the plate/screw interface. The screw nut provides more secure fixation by substituting for the stabilizing effect that the near cortex would normally provide when it is securely fastened to the plate. This scenario also may occur when a 4.5 mm drill bit is accidently used to make the hole for a 4.5 mm cortical screw and the near cortex is violated, or when a hole at the near cortex is stripped by inadvertently over-tightening a screw that is too short.

If a screw is used to lag a butterfly fragment to the plate, cycled loads will cause the screw to back out due to the forces that become present that are coaxial to the screw shaft. Such forces will cause the screw to loosen due to the effect of loading the inclined plane of the threads. This is rendered more susceptible when the fragment is not able to be fixed securely to the plate, since this allows toggle to occur at the plate/screw interface. The screw nut locks the screw to the plate, thus preventing the backing out of the screw, and provides added stability by holding the fragment in a fixed position with respect to the plate.

When tightened, the screw is secured to the plate in a fixed orthogonal position, similar to the situation that is present when a pin is clamped to an external fixator frame. With the screw(s) thus fixed to the plate and bone, several enhancements become evident. First, in osteoporotic bone or bone with thin cortices, early loosening due to cycled loads is avoided, since the screws are fixed to the plate, rendering them exempt from the effects of toggling at the plate/screw interface.

The screw nut acts as a mechanical cortical substitute in situations where bone is lost at the near cortex due to trauma or disease. Once the bone screw is locked by the screw nut, any bone fragment held by the bone screw will be fixed in space, since toggle of the screw with the plate will be eliminated. Therefore, if a portion of bone is deficient adjacent to the bone plate, the surgeon can still place a screw through the opposite cortex, allowing fixation to be distributed over a greater portion of the plate.

The screw nut allows the bone screw to store some of the energy that is used when generating compression at a fracture or osteotomy site. This will provide compression that lasts longer than that provided by a plate with screws, since cycled loads can lead to loosening. This effect is analogous to the preload and compression that is achieved with a ninety degree blade plate.

The screw nut is a valuable asset to the surgeon's armamentarium when faced with complex fractures or deformity. The ability to convert any portion of a plate into a "fixed pin" device increases the versatility with which internal fixation may be applied. If a bone fragment is not able to be apposed to the plate when the screw is tightened, toggle is possible at the plate/screw interface with a resultant decrease in the overall stability. The screw nut rigidly fixes the screw so that the bone fragment is held in a more restrained manner. This effect has been loosely termed the "locked lag technique".

The various features of novelty which characterize the invention are pointed out with particularity in the claims annexed to and forming part of this disclosure. For the better understanding of the invention, its operating advantages and specific objects attained by its use, reference should be had to the accompanying drawings and descriptive matter in which are illustrated and described preferred embodiments of the invention.

BRIEF DESCRIPTION OF THE DRAWINGS

In the drawings

As shown in FIGS. 1 and 2 the screw nut according to the invention consists basically of a single-piece body 5, 6 with a central axis 2, a central hole 3 with a hole axis 34 and with an internal thread 4 able to receive the bone screw 15 shown in FIG. 4, a lower section 5, an upper section 6, a lower side 9 and an upper side 10.

Figure 1:
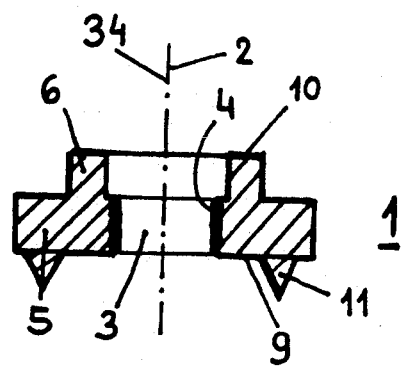
FIG. 1 is an axial section through the screw nut according to the invention with sharp projections oriented to the bone contact area.

The profile 7 of the upper section 6 orthogonal to the axis 2 is smaller than the profile 8 of the lower section 5 orthogonal to the axis 2. Further the upper section 6 is shaped in such a way, that it is insertable into the plate hole 21 of the bone plate 20 shown in FIG. 5. To this purpose the circular cylindrical upper section 6 is flattened on two opposite sides as shown in FIG. 2 so as to obtain approximately an elliptical profile with axis of approx. 7.0 to 5.28 mm.

This flattened upper section 6 can now be introduced rotatively fixed into the usual standardized holes 21 of usual bone plates 20 (FIG. 5) from the under side 24. The axial height of the upper section 6 is 1.5 mm. The axial height of the lower section 5 is approximately 2.0 mm. The diameter of the central hole 3 is 4.5 mm. On the underside 9 located in the lower section 5 of the screw nut 1 there are four projections 11 in the form of sharp pins which are disposed at 90° angles. Instead of four projections 11 it is possible to adopt any other number, e.g. three projections 11 which are staggered by 120°.

Figure 2:
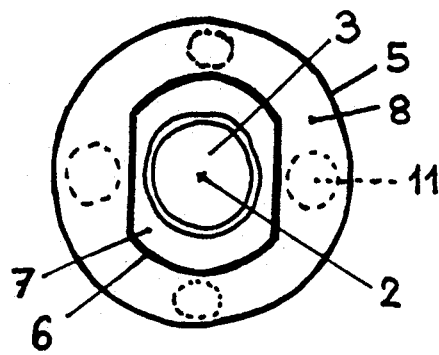
FIG. 2 is a top view of the screw nut according to FIG. 1.

The internal thread 4 is threaded directly in the inner surface of the central hole 3 (FIGS. 1 and 2). Central axis 2 and hole axis 34 coincide in this symmetrical embodiment of the screw nut 1.

Figure 9:
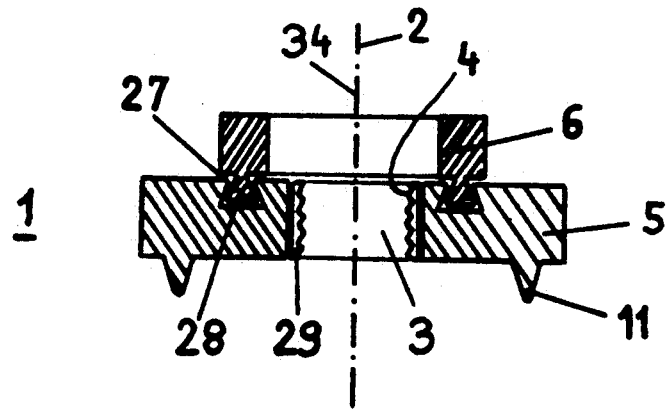
FIG. 9 is an axial section through a further embodiment of the screw nut according to the invention consisting of two pieces.

As shown in FIG. 9 the screw nut 1 can also be made of two separate parts in such a way that the lower section 5 rotates around the axis 2 with respect to the upper section 6. This is achieved by a circular groove 28 having a dove-tail configuration in the lower section 5 and a corresponding circular rim 27 having dove-tail configuration in the upper section 6.

Figure 3:
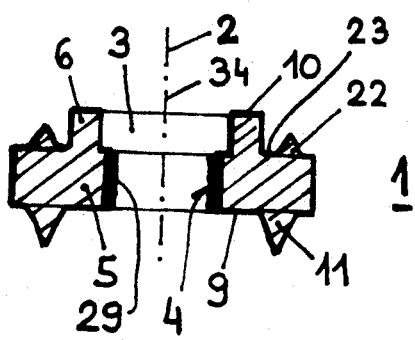
FIG. 3 is an axial section through a modified screw nut according to the invention with pins oriented to the bone contact area as well as to the plate contact area.

In a further embodiment represented in FIG. 3 the screw nut 1 according to the invention has generally the same construction as in the embodiment according to the FIGS. 1 and 2. Differently from the latter, however, the lower section 5 is provided at its free upper side 23 with four projections 22 in the form of sharp edges or pins. The projections 11 as well as the projections 22 are disposed symmetrically with respect to the central axis 2, they are staggered by 90° each. The internal thread 4 in this embodiment consists of an insert element 29 made of plastics. By this means an improved anchoring of the bone screw 15 (FIG. 4) is achieved. The basic body 5, 6 of the screw nut 1 consists in this embodiment of a memory alloy which adopts a smaller volume when it is heated from lower temperatures to body temperature.

Figure 4:
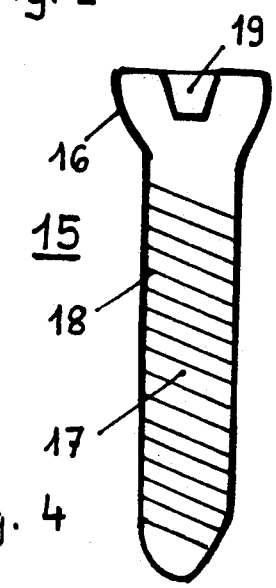
FIG. 4 is a schematic view of a bone screw for use with the screw nut according to FIG. 1.

In FIG. 4 a bone screw 15 according to prior art is represented with a head 16 and a shaft 18. The head 16 has a hexagonal recess 19 into which a suitable instrument can be inserted. The shaft 17 has an external thread 18 which corresponds to the internal thread 4 of the central hole 3 of the screw nut 1.

Figure 5:
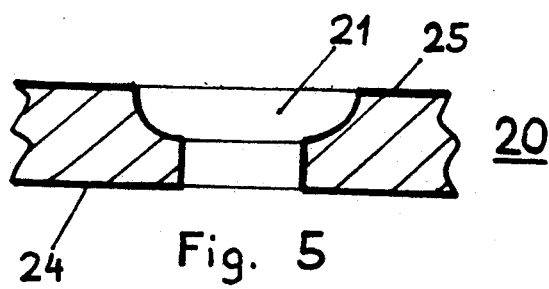
FIG. 5 is a partial longitudinal section through a bone plate for use with a bone screw according to FIG. 1.

FIG. 5 represents a conventional bone plate 20 with its under side 24 and its upper side 25 which is traversed by holes 21. The plate has a thickness of approximately 4.5 mm.

Figure 6:
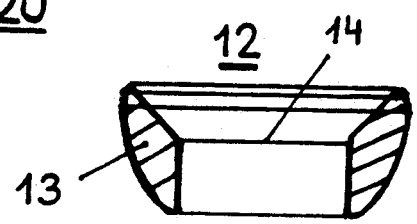
FIG. 6 is an axial section through a bushing for use with the screw nut according to FIG. 1.
Figure 7:
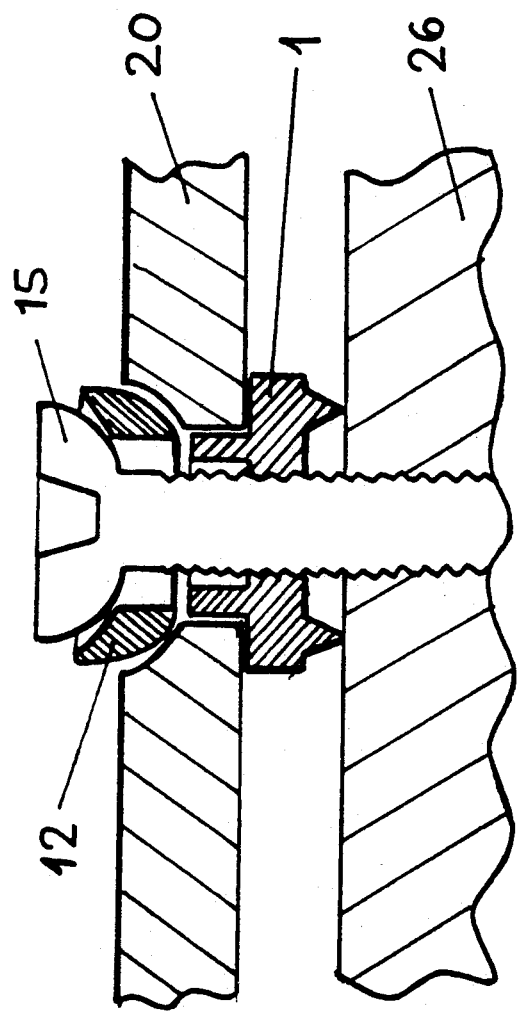
FIG. 7 is a partial longitudinal section through a fixation assembly with a screw nut according to FIG. 1, a bone plate according to FIG. 5, a bone screw according to FIG. 4 and a bushing according to FIG. 6.

In FIG. 7 a fixation assembly is partially represented which is fixed to the bone 26. It consists of a screw nut 1, a bone plate 20, as well as several bone screws 15 of which only one is represented in the figure. The screw nut 1 abuts to the under side of the bone plate 20 and acts as a distance holder between bone 26 and bone plate 20 by means of its pins 11 oriented to the bone 26. Between the head 16 of the bone screw 15 and the upper side 25 of bone plate 20 a bushing 12 is placed which can be inserted at choice. The bushing 12, represented in detail in FIG. 6, consists essentially of a semispherical section 13 with a central bore 14 into which the bone screw 15 is insertable. The outer shape of section 13 is designed in such a way that the bushing 12 is easily insertable into the standardised holes 21 of the usual bone plates 20. The axial height of the bushing 12 is about 3.6 mm; its smallest diameter is 4.6 mm and its maximum diameter is 8.0 mm. The bushing 12 is designed to fit the convexity of the screw head 16 and also to fit in the concavity of the holes 21 in the bone plate 20.

Figure 8:
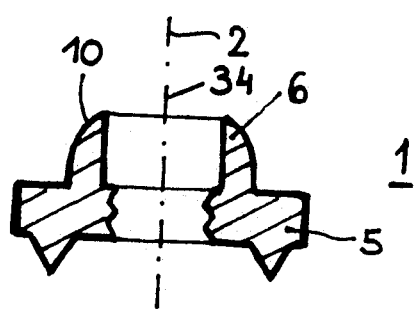
FIG. 8 is an axial section through a further embodiment of the screw nut according to the invention.

In FIG. 8 a further embodiment of the screw nut 1 according to the invention is represented in which the upper section 6 is designed in such a way that it can adopt the function of the bushing 12 according to FIG. 6. The section 6 is rounded at its upper side 10 in order to allow a certain rotation of the spherical screw head 16 of the screw 15 according to FIG. 4. By this construction the direction of the screw 15 can be tilted with respect to the central axis 2 within certain limits.

Figure 10:
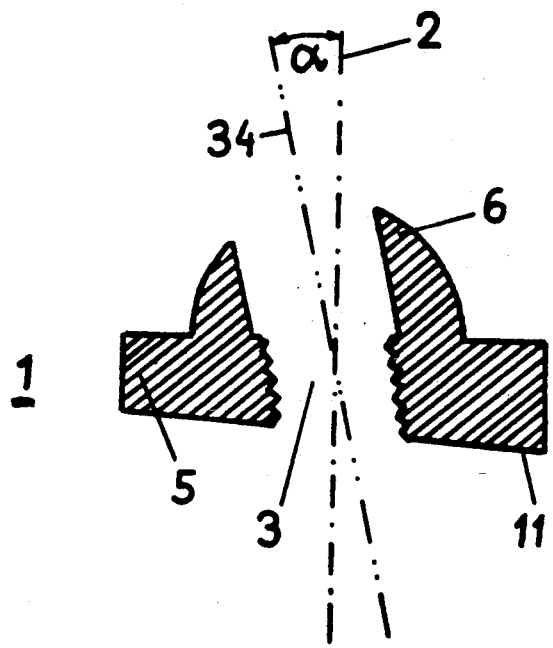
FIG. 10 is an axial section through a further embodiment of the asymmetrical screw nut according to the invention.

In FIG. 10 a further embodiment of the screw nut 1 according to the invention is represented in which the axis 34 of the central bore 3 intersects with an angle α with the central axis 2 of the body 5,6. The upper section 6 is similar to the embodiment according to FIG. 8 but asymmetrical due to the inclined bore hole 3. The lower section 5 is not provided with sharp-edged pins as in the afore described embodiments, but instead with a wedge 11. The wedge 11 is disposed asymmetrically with respect to the central axis 2 and serves two purposes, namely first to provide for adaptation of the screw nut to the bone surface and second for varying the direction of the bone screw to be inserted.

Figure 11:
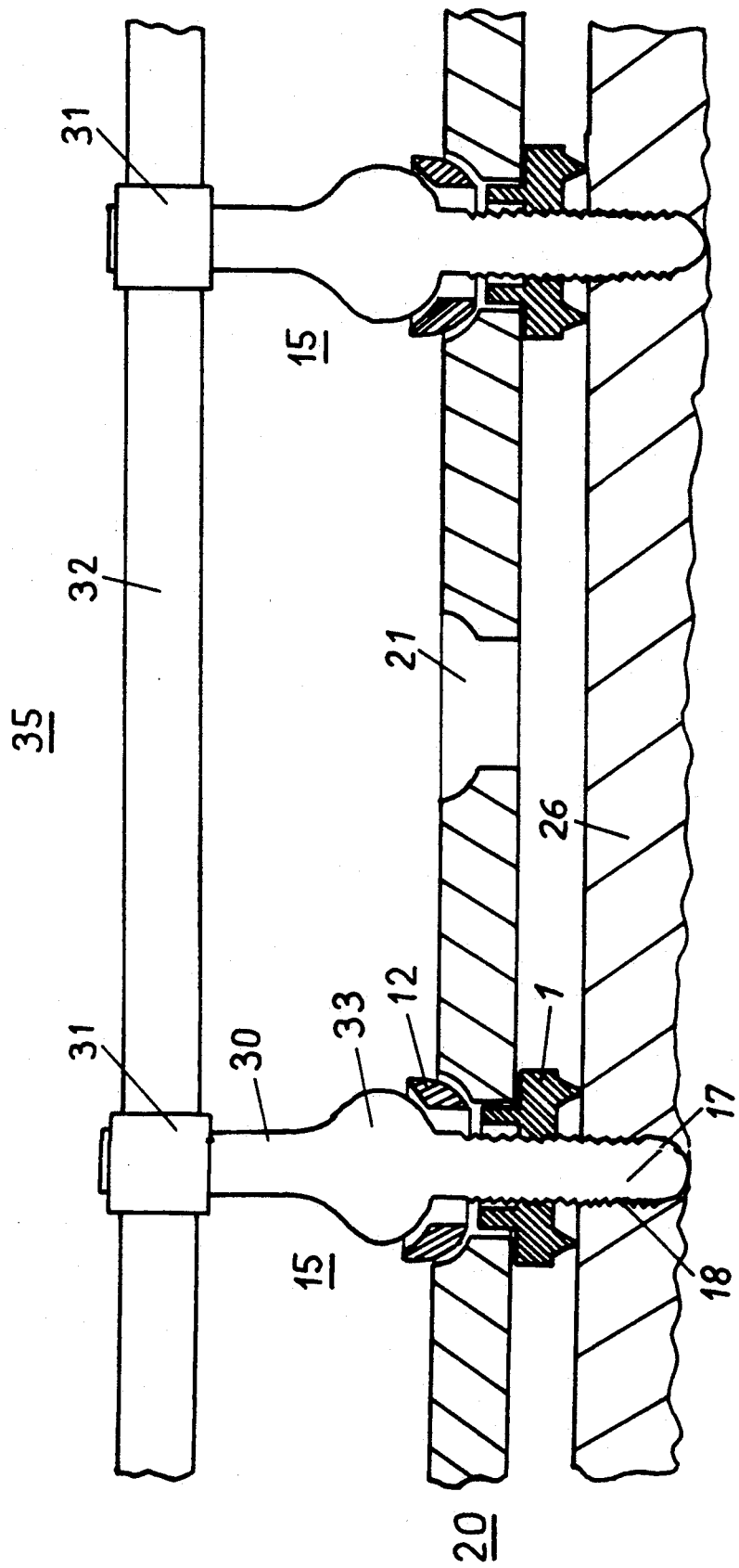
FIG. 11 is a partial longitudinal section through a fixation assembly with two screw nuts according to FIG. 1, a bone plate according to FIG. 5, two bushings according to FIG. 6 and two modified bone screws.

FIG. 11 shows how to create a fixation assembly 35 by using modified bone screws 15 having a rod 30 projecting axially from a modified head 33. By using two or more such modified bone screws 15 secured to a bone plate 20 by means of screw nuts 1 and bushings 12—similar to the application according to FIG. 7—it is possible to attach a longitudinal bar 32 on the bars 30 by means of clamps 31, thereby producing a fixation assembly 35 rigidly anchored to the bone 26. The length of the bar 30 is approximately between 80 and 120 mm; its diameter is between 5 and 6 mm. The diameter of the screw shaft 17 having the threads 18 is 4.5 mm and its length is about 25 to 60 mm. The plate hole 21 of plate 20 can be left free or can be used to accommodate an unmodified screw according to FIG. 4.

When combining the screw nut with prior art screws and plates care should be taken to use identical materials in order to avoid the formation of galvanic elements which can lead to corrosion.

I claim:

1. An assembly for the internal fixation of bones comprising a bone plate having an upper surface, a lower surface shaped for positioning adjacent a bone to be treated, and a screw hole for accommodating a bone screw, in combination with a nut for fixing a bone screw to said plate, said nut having a central axis, a through hole extending along said axis, a lower section and an upper section, said upper section having a cross section orthogonal to said axis smaller than the cross section of said lower section orthogonal to said axis, thus to form a shoulder at the junction of said upper and lower sections, the upper section of the nut and the plate hole being shaped to coaptly join one another, with said shoulder abutting the lower surface of said plate, at least a part of the through hole of said nut being threaded, to engage a bone screw inserted in the hole in said plate.

2. The assembly claimed in claim 1, wherein the cross-section of the upper section of the nut has a shape which enables it to be inserted rotationally fixed into said plate hole of said bone plate.

3. The assembly claimed in claim 2, wherein the cross-section of the upper section of the nut orthogonal to said hole axis is generally elliptical.

4. The assembly claimed in claim 2 wherein the lower side of the lower section of said nut is provided with projection means for locking the nut to an abutting bone surface.

5. The assembly claimed in claim 1, wherein the lower section and the upper section of the nut comprise two separate elements connected to one another by means allowing rotation with respect to said central axis.

6. The assembly claimed in claim 2, wherein said internal thread is in part made of plastics.

7. The assembly claimed in claim 2, wherein said nut comprises a memory alloy which adopts a smaller volume when heated from lower temperatures to body temperature.

8. The assembly claimed in claim 1, wherein the lower section of said nut is provided on the lower side with projection means for locking the nut to an abutting surface.

9. The assembly according to claim 4 or 8, wherein said projections are located symmetrically around said central axis.

10. The assembly claimed in claim 4 or 8, wherein the projections are located asymmetrically around said central axis.

11. The assembly claimed in claim 1, wherein the central axis and the hole axis are identical.

12. The assembly claimed in claim 1, wherein said central axis and said hole axis intersect.

13. The assembly claimed in claim 2 and further comprising a screw having a head and a bushing seated in the screw hole in said plate at the upper surface of said plate, said bushing having an upper surface shaped to match the head of said screw.

14. The assembly claimed in claim 1, wherein the cross-section of said upper section orthogonal to said hole axis has a generally rectangular shape.

15. The assembly claimed in claim 4, wherein the projections are in the form of pins.

16. The assembly claimed in claim 4, wherein the projections are in the form of wedges.

17. The assembly claimed in claim 6, wherein the screw thread is a hollow cylindrical insert.

18. The assembly claimed in claim 8, wherein the projections are pins.

19. The assembly claimed in claim 8, wherein the projections are wedges.

* * * * *